(12) United States Patent
Burd et al.

(10) Patent No.: US 7,674,277 B2
(45) Date of Patent: Mar. 9, 2010

(54) SIDE-LOADING BONE ANCHOR

(75) Inventors: Brian A. Burd, Memphis, TN (US); Matthew M. Morrison, Cordova, TN (US)

(73) Assignee: Warsaw Orthopedic, Inc.

( * ) Notice: Subject to any disclaimer, the term of this patent is extended or adjusted under 35 U.S.C. 154(b) by 1401 days.

(21) Appl. No.: 11/000,846

(22) Filed: Dec. 1, 2004

(65) Prior Publication Data

US 2006/0116677 A1 Jun. 1, 2006

(51) Int. Cl.
*A61B 17/70* (2006.01)

(52) U.S. Cl. .................. 606/265; 606/266; 606/269; 606/270

(58) Field of Classification Search ........... 606/69–73, 606/264–270, 300–308
See application file for complete search history.

(56) References Cited

U.S. PATENT DOCUMENTS

| | | |
|---|---|---|
| 4,641,636 A | 2/1987 | Cotrel |
| 4,815,413 A | 3/1989 | Kota |
| 5,005,562 A | 4/1991 | Cotrel |
| 5,067,955 A | 11/1991 | Cotrel |
| 5,487,742 A | 1/1996 | Cotrel |
| 5,534,002 A * | 7/1996 | Brumfield et al. ............. 606/61 |
| 5,578,033 A | 11/1996 | Errico et al. |
| 5,584,834 A | 12/1996 | Errico et al. |
| 5,601,552 A | 2/1997 | Cotrel |
| 5,603,714 A * | 2/1997 | Kaneda et al. ................ 606/61 |
| 5,609,594 A | 3/1997 | Errico et al. |
| 5,669,911 A * | 9/1997 | Errico et al. .................. 606/61 |
| 5,690,630 A | 11/1997 | Errico et al. |
| 5,733,285 A | 3/1998 | Errico et al. |
| 5,797,911 A | 8/1998 | Sherman et al. |
| 5,817,094 A | 10/1998 | Errico et al. |
| 5,885,286 A | 3/1999 | Sherman et al. |
| 5,989,250 A | 11/1999 | Wagner et al. |
| 6,063,090 A | 5/2000 | Schlaepfer et al. |
| 6,132,430 A | 10/2000 | Wagner |
| 6,280,442 B1 | 8/2001 | Barker et al. |
| 6,416,515 B1 | 7/2002 | Wagner |
| 6,485,491 B1 | 11/2002 | Farris et al. |
| 6,562,040 B1 | 5/2003 | Wagner |

(Continued)

FOREIGN PATENT DOCUMENTS

EP 0 553 042 A1 7/1993

(Continued)

OTHER PUBLICATIONS

Medtronic Sofamor Danek, Inc.; "Medtronic Sofamor Danek Product Catalog"; pp. A-38, A-39, 2000.

*Primary Examiner*—Thomas C Barrett
*Assistant Examiner*—Andrew Yang

(57) ABSTRACT

A side-loading bone anchor is provided, which may be used in cervical, thoracic, lumbar or sacral areas of the spine or other orthopedic locations. In one embodiment, the anchor includes an anchoring portion and a receiving portion. The anchoring portion is attached to a bone, and is connected to the receiving portion. A rod or other elongated support member is received in the receiving portion in contact with a crown member in the receiving portion and above the anchoring portion. The receiving portion, with or without the rod, may be rotated or pivoted with respect to the anchoring portion, and a set screw is threaded into the receiving portion to lock the rod within the receiving portion.

21 Claims, 8 Drawing Sheets

U.S. PATENT DOCUMENTS

| | | | |
|---|---|---|---|
| 7,087,057 B2 * | 8/2006 | Konieczynski et al. | 606/73 |
| 7,175,624 B2 * | 2/2007 | Konieczynski et al. | 606/71 |
| 7,278,995 B2 * | 10/2007 | Nichols et al. | 606/272 |
| 2001/0047173 A1 * | 11/2001 | Schlapfer et al. | 606/72 |
| 2003/0149435 A1 * | 8/2003 | Baynham et al. | 606/72 |
| 2005/0222570 A1 * | 10/2005 | Jackson | 606/72 |

FOREIGN PATENT DOCUMENTS

| | | |
|---|---|---|
| EP | 1 210 914 A | 6/2002 |

* cited by examiner

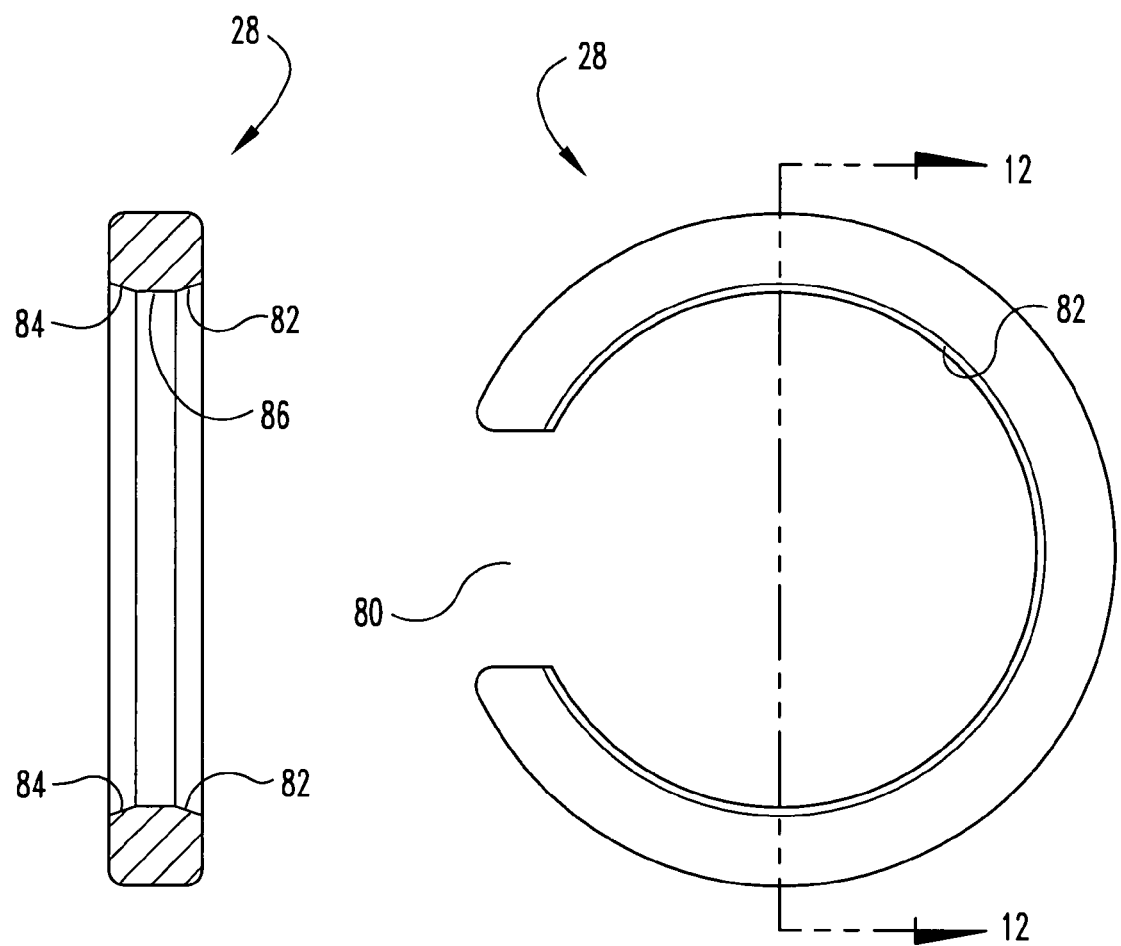
Fig. 12  Fig. 11

SIDE-LOADING BONE ANCHOR

BACKGROUND OF THE INVENTION

The present invention concerns bone anchors, particularly useful for engagement in the vertebrae. In a particular embodiment, the invention contemplates a bone screw assembly that allows loading of an elongated rod or other member extending along the spine from the side.

Several techniques and systems have been developed for correcting and stabilizing the spine and for facilitating fusion at various levels of the spine. In one type of system, a bendable rod is disposed longitudinally along the length of the spine or vertebral column. The rod may be preferably bent to correspond to the normal curvature of the spine in the particular region being instrumented. For example, the rod can be bent to form a normal kyphotic curvature for the thoracic region of the spine, or a lordotic curvature for the lumbar region. In accordance with such a system, the rod is engaged to various vertebrae along the length of the spinal column by way of a number of fixation elements. A variety of fixation elements can be provided which are configured to engage specific portions of the vertebra. For instance, one such fixation element is a hook that is configured to engage the laminae of the vertebra. Another very prevalent fixation element is a spinal screw which can be threaded into various aspects of the vertebral bone.

In one typical procedure utilizing a bendable rod, the rod is situated on one or opposite sides of the spine or spinous processes. A plurality of bone screws are threaded into a portion of several vertebral bodies, for example into the pedicles of these vertebrae. The rod(s) are connected or affixed to these plurality of bone screws to apply corrective and stabilizing forces to the spine.

One example of a rod-type spinal fixation system is the TSRH® Spinal System sold by Medtronic Sofamor Danek, Inc. The TSRH® System includes elongated rods and a variety of hooks, screws and bolts all configured to create a segmental construct throughout the spine. In one aspect of the TSRH® System, the spinal rod is connected to the various vertebral fixation elements by way of an eyebolt. In this configuration, the fixation elements are engaged to the spinal rod laterally adjacent to the rod. In another aspect of the TSRH® System, a variable angle screw is engaged to the spinal rod by way of an eyebolt. The variable angle screw allows pivoting of the bone screw in a single plane that is parallel to the plane of the spinal rod. Details of this variable angle screw can be found in U.S. Pat. No. 5,261,909 to Sutterlin et al., owned by the Assignee of the present invention. One goal achieved by the TSRH® System is that the surgeon can apply vertebral fixation elements, such as a spinal hook or a bone screw, to the spine in appropriate anatomic positions. The TSRH® System also allows the surgeon to easily engage a bent spinal rod to each of the fixation elements for final tightening.

Another rod-type fixation system is the Cotrel-Dubosset/CD Spinal System sold by Medtronic Sofamor Danek, Inc. Like the TSRH® System, the CD® System provides a variety of fixation elements for engagement between an elongated rod and the spine. In one aspect of the CD® System, the fixation elements themselves include a body that defines a slot within which the spinal rod is received. The slot includes a threaded bore into which a threaded plug is engaged to clamp the rod within the body of the fixation element. The CD® System includes hooks and bone screws with this "open-back" configuration. Details of this technology can be found in U.S. Pat. No. 5,005,562 to Cotrel. One benefit of this feature of the CD® System is that the fixation element is positioned directly beneath the elongated rod. This helps reduce the overall bulkiness of the implant construct and minimizes the trauma to surrounding tissue.

These and other vertebral anchors have channels for an elongated rod or other member that open upward, i.e. directly away from the bone to which the anchor is attached. The convenience of such a structure is clear, as the anchor can be first placed in the bone, then the rod can be essentially lain on top of it, within the channel. In many cases, however, a surgeon may wish to use anchors to translate the vertebral body to the rod. This translation will typically involve horizontal as well as vertical components. Side loading implants, along with their associated instruments, can simplify the execution of this type of maneuver. Use of such implants can present less interference from lateral tissue, the potential to pre-load the locking components prior to inserting the anchor and also innovative means of provisionally capturing the rod prior to final tightening.

To address these issues, bone anchors having a channel opening to the side have been developed. However, new and improved side-loading bone anchors are still needed in the industry.

BRIEF DESCRIPTION OF THE FIGURES

FIG. 11 is a top view of an embodiment of a clip member of the embodiment shown in FIG. 1.

FIG. 12 is a cross-sectional view taken along the lines 12-12 in FIG. 11 and viewed in the direction of the arrows.

DESCRIPTION OF A PREFERRED EMBODIMENT

Figure 1:
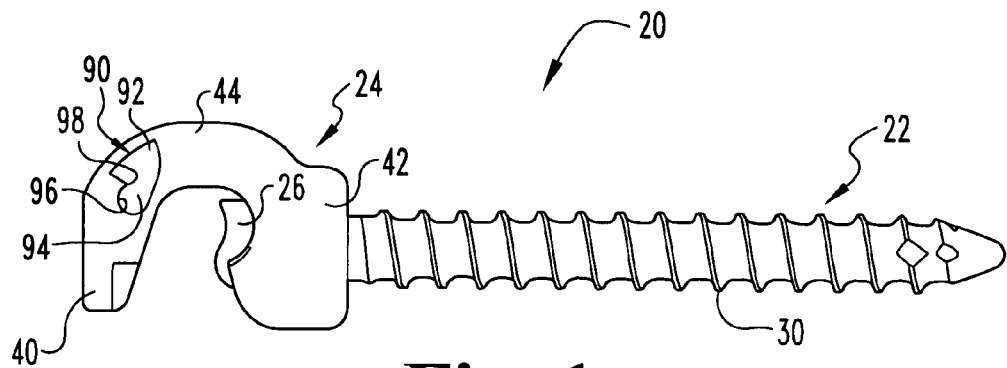
FIG. 1 is a side view of an embodiment of a side-loading bone anchor.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

Figure 2:
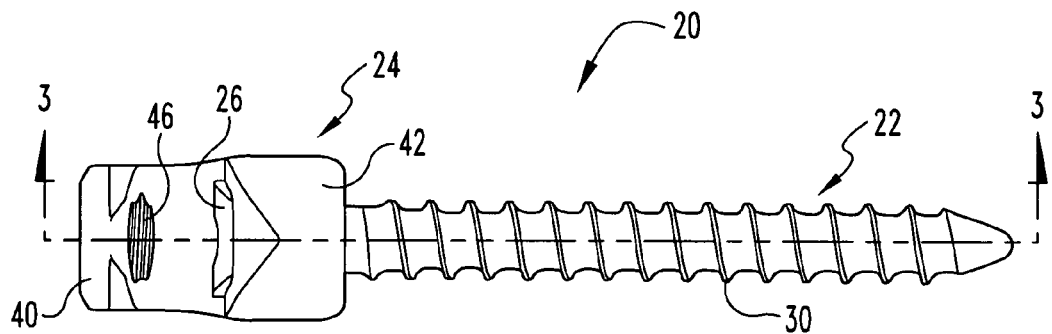
FIG. 2 is a side view of the embodiment shown in FIG. 1, rotated ninety degrees with respect to FIG. 1.
Figure 3:
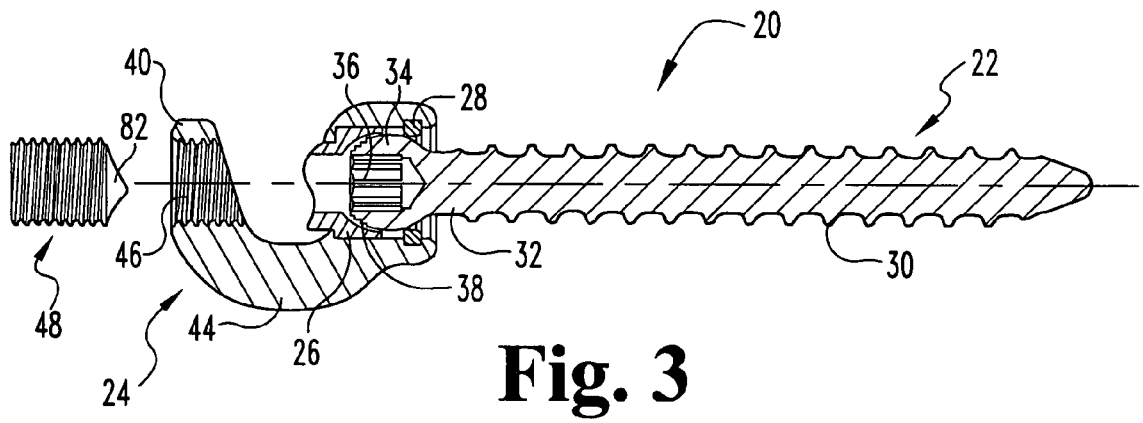
FIG. 3 is a cross-sectional view taken along the lines 3-3 in FIG. 2 and viewed in the direction of the arrows.
Figure 4:
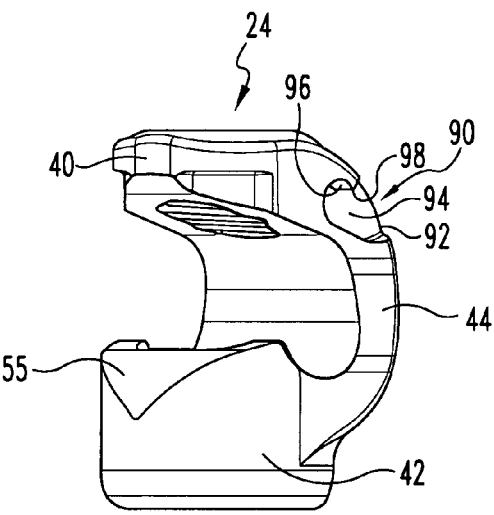
FIG. 4 is a perspective view of an embodiment of a receiving portion of the embodiment shown in FIG. 1.
Figure 5:
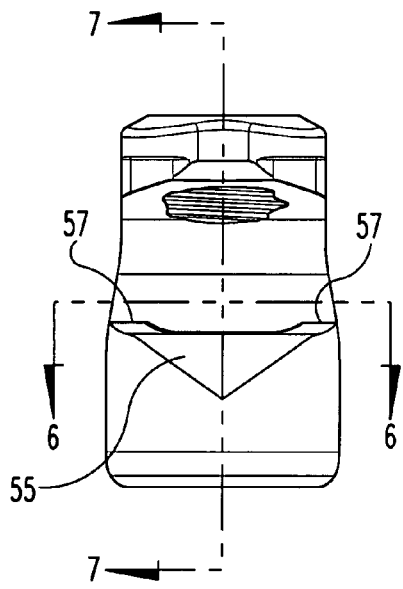
FIG. 5 is a side view of a portion of the embodiment shown in FIG. 1.
Figure 7:
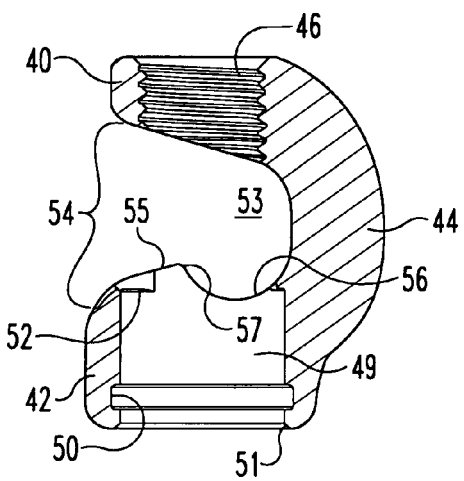
FIG. 7 is a cross-sectional view taken along the lines 7-7 in FIG. 5 and viewed in the direction of the arrows.
Figure 6:
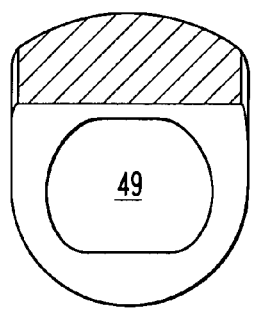
FIG. 6 is a cross-sectional view taken along the lines 6-6 in FIG. 5 and viewed in the direction of the arrows.
Figure 10:
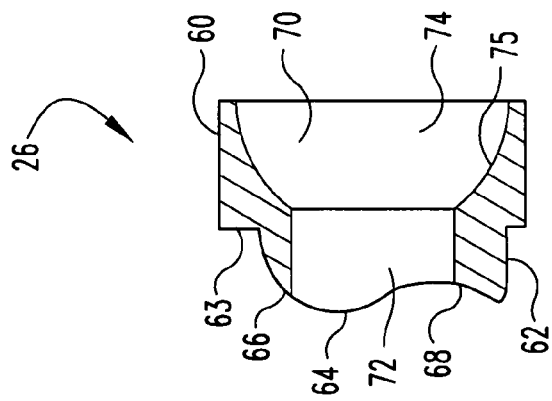
FIG. 10 is a cross-sectional view taken along the lines 10-10 in FIG. 9 and viewed in the direction of the arrows.
Figure 9:
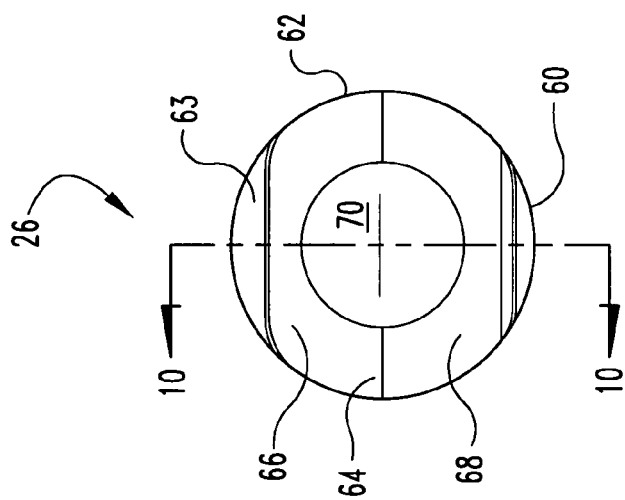
FIG. 9 is a top view of the embodiment of FIG. 8.
Figure 8:
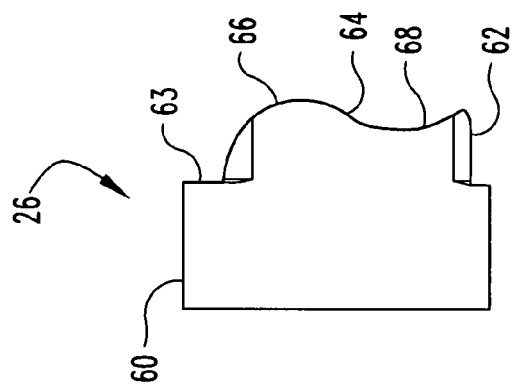
FIG. 8 is a side view of an embodiment of a crown member of the embodiment shown in FIG. 1.
Figure 16:
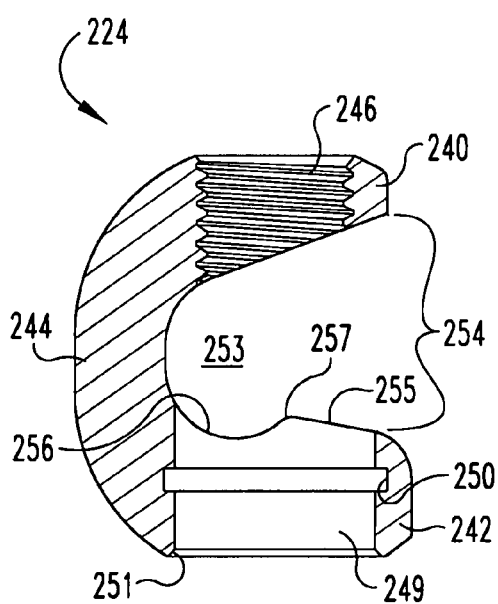
FIG. 16 is a cross-sectional view taken along the lines 16-16 in FIG. 13 and viewed in the direction of the arrows.

Looking first at FIGS. 1-3, there is shown an embodiment of a side-loading bone screw 20. Bone screw 20 may be made for attachment to vertebrae, such as cervical, thoracic, lumbar and or sacral bone structures, or other bones or tissues. Similarly, aspects of bone screw 20 described herein can be included in vertebral hooks, bone clamps, and other orthopedic implant devices.

Screw 20, in the embodiment shown in FIG. 1, includes a shaft portion 22, a receiving portion 24, a crown member 26 and a clip 28. Shaft 22 is an elongated piece having one or more threads 30 on at least a portion, e.g. a relatively lower portion. Thread 30 may be a cancellous thread, of a configuration suited to implantation into a vertebra or similar bone. Thread 30 may be self-tapping or intermittent, or may have more than one crest winding about shaft 22, or of other appropriate configurations. A neck 32 at a relatively upper portion of shaft 22 is provided. Neck 32 may be above thread 30, or may also include thread(s) or a threaded portion. Shaft portion 22 further includes a head portion 34. Head portion 34 is at least part spherical in one embodiment, having an imprint 36 in a top of head 34. Imprint 36 may be hexagonal, hexalobed, or of other appropriate shape. One or more ridges 38 may be provided, and in one embodiment ridge(s) 38 may be concentric with imprint 36.

Referring now additionally to FIGS. 4-7, the depicted embodiment of receiving portion 24 is substantially C-shaped, having an upper leg 40, a base 42, and an intermediate portion 44 joining them. Upper leg 40 has a threaded aperture 46 into which a set screw 48 can be threaded. Aperture 46 may have a longitudinal axis that is perpendicular to upper leg 40, or such axis may be angled with respect to upper leg 40, e.g. toward intermediate portion 44.

Base 42 includes a hole 49 therethrough. Hole 49 is at least partially substantially cylindrical in one embodiment, having a longitudinal axis, a diameter at least slightly greater than the diameter of head portion 34, and a depth at least slightly greater than the height of head portion 34. In one particular embodiment, leg 40 has an underside that is obliquely angled with respect to the axis of hole 49. Thus, as a rod is loaded from the side of receiving portion 24, as further described below, the rod's general direction may be substantially perpendicular to the axis of hole 49, e.g. within ten to twenty degrees of a line perpendicular to the axis of hole 49. Near a lower end of base 42, a groove 50 is provided. Groove 50, in the illustrated embodiment, is of substantially constant depth and width, and is around all or substantially all of hole 49. Hole 49 further may include a substantially conical opening 51 at a lower end of base 42, and an abutment or flange 52 near an upper end of hole 49.

Clip member 28 is substantially C-shaped, with a gap 80 allowing clip 28 to be elastically expandable and contractible. Clip 28 is sized to fit at least partially within groove 50 when clip member is in an unstressed, i.e. unexpanded and uncontracted, state. Clip 28 may have conical portions 82 and 84 on upper and lower portions and a substantially cylindrical intermediate portion 86. Clip 28 has an internal dimension that is at least slightly smaller than the diameter of head portion 34 of shaft portion 22, but larger than neck 32, and an external dimension that allows clip 28 to fit at least partially within groove 50. In one embodiment, the unstressed external dimension of clip 28 is at least slightly larger than the diameter of groove 50, so that when clip 28 is within groove 50, clip 28 is in an at least slightly compressed state.

Intermediate portion 44 joins leg 40 and base 42. Taken together, leg 40, base 42 and intermediate portion 44 form substantially a C-shape, with a channel 53 substantially to one side of intermediate portion 44 having a mouth 54 between leg 40 and base 42. In a particular embodiment, mouth 54 is somewhat wider than the breadth of channel 53 further within receiving portion 24. For example, base 42 may include a surface 55 sloping somewhat toward leg 40, and as already noted an underside of leg 40 may slope down toward intermediate portion 44. Channel 53 in an area adjacent to base 42 and intermediate portion 44 has a substantially cylindrical portion 56, and channel 53 communicates with hole 49. Surface 55 may meet cylindrical portion 56 at one or more ridges 57.

Crown member 26 has a generally cylindrical side exterior that fits slidably within hole 49 of receiving portion 24. In a particular embodiment, crown member 26 has a lower generally cylindrical portion 60 and an upper generally cylindrical portion 62 that is of at least slightly smaller diameter than portion 60, forming an abutment or flange 63. Upper portion 62 includes a top surface 64 that undulates. For example, one side of upper portion 62 has a substantially part-cylindrical convex surface 66, which is joined to a substantially part-cylindrical concave surface 68 on the other side of upper portion 62. In certain embodiments, concave surface 68 may have a radius of curvature approximating that of a rod to be connected to screw 20, and convex surface 66 may have a radius of curvature slightly less than that of concave surface 68. An aperture 70 extends through crown member 26. An upper portion 72 of aperture 70 is substantially cylindrical, and a lower portion 74 of aperture 70 has a substantially part-spherical surface. Upper portion 72 is sized to permit a tool to be extended through it to engage imprint 36 in head portion 34 of shaft portion 22. Lower portion 74 has an internal diameter approximately the same or at least slightly larger than the diameter of head portion 34, to allow head portion 34 to be multi-axially positionable when head portion 34 of shaft portion 22 is adjacent lower portion 74 of aperture 70 of crown member 26.

In addition to the features of the embodiment described above, receiving portion 24 may further include one or more indentations 90 for receiving a gripping or positioning tool. Indentations 90 are shown in one embodiment on either side of receiving portion 24, in an area in or adjacent to upper leg 40 and/or intermediate portion 44. It will be seen that indentations 90 could be in any part of receiving portion 24. Indentations 90 in the illustrated embodiment have an entry portion 92 and a holding portion 94. Holding portion 94 has a rounded or part circular portion 96 having a corner 98. A holding or gripping tool (not shown) having one or more rounded or circular protrusions at or adjacent to the end(s) of such a tool may be used. Such protrusion(s) may be inserted in a first direction at entry portion(s) 92 and curved, angled or hooked around corner 98 into circular portion 96. In this manner, such a tool can be used to hold, position, manipulate or otherwise work on or with screw 20.

In assembling screw 20, crown member 26 is inserted into hole 49 in receiving portion 24 through lower opening 51 so that upper portion 62 at least partially extends from hole 49 into channel 53. Crown member 26 may be inserted far enough so that abutment 63 of crown member 26 is adjacent to or contacts abutment 52 in hole 49. Crown member 26 may be positioned so that convex surface 66 is relatively forward, i.e. between concave surface 68 and mouth 55 of receiving portion 24, and so that concave surface 68 is between convex surface 66 and intermediate portion 44 of receiving portion 24. Convex surface 68 in that position may be adjacent ridge (s) 57. Head portion 34 of shaft portion 22 is inserted into hole 49 via opening 51 so that head portion 34 is adjacent crown member 26. Clip 28 is drawn up around threaded portion 30 of shaft portion 22 and inserted through opening 51 into groove 50. In one embodiment, shaft portion 22 can be first inserted through clip 28, and the combination can be inserted into hole 49 so that head portion 34 is adjacent crown member 26 and clip 28 is at least partially within groove 50. In another embodiment, shaft portion 22 can first be inserted into hole 49, followed by clip 28.

Assembly of screw 20 as noted above may be done during or soon after the manufacturing process of the individual components. If done in that way, then the surgeon is provided an assembly including receiving portion 24 with crown member 26, shaft 22 and clip 28 connected as described above. One or more sizes of such assemblies can be provided in a kit so that the surgeon can select the appropriate assembly. Set screws, such as set screw 48, may also be provided with such assemblies. Such a set screw 48 includes external threads adapted for engagement with threaded aperture 46, and may include an internal or external imprint (not shown) in or on a top surface adapted for engagement with a tool for tightening and/or loosening set screw 48. It will be seen that an internal print may be preferred as it may add nothing or a smaller amount to the overall height or profile of screw 20. Set screw 48 may further include a curved, pointed, conical or other surface 82 at the bottom. Such a surface engages a rod within receiving portion 24 as further described below. Set screw 48 may be placed at least partially within threaded aperture 46 such that none or a very small amount of set screw 48 extends into channel 53. Alternatively, set screw 48 may be left out of aperture 46 until a rod is inserted into receiving portion 24, and may then be inserted into aperture 46 and against the rod, as is further described below. Individual parts may also be provided to the surgeon, who can assemble the assemblies as indicated above.

In use, a surgeon first prepares the surgical site as is generally known in the art, for example by making an open, minimally-invasive or other incision in the skin and subdermal tissues to obtain access to the desired surgical site. In this description, spinal surgery will be described as a principal example of the use of the above-described embodiments. Once access to a vertebra has been obtained, the surgeon prepares a hole in the vertebra. Screw 20 is then introduced to the surgical site, and threaded portion 30 may be threaded or otherwise inserted into the hole in the vertebra. A holding tool (not shown) with protrusions connected to anchor 20 via indentations 90 can be used to hold screw 20, and particularly shaft 22, proximate to a hole in the vertebra. It will be seen that if shaft 22 is self-tapping, then it will not be necessary to tap or otherwise thread the hole in the vertebra.

A tool (not shown) for inserting the shaft is maneuvered into contact with imprint 36 of shaft 22. In an embodiment in which aperture 46 is substantially aligned with hole 49, the tool can be inserted through aperture 46 of leg 40, channel 53 and aperture 70 of crown member 26 and into contact with shaft 22. The tool is then used to insert shaft 22 into the bone, e.g. by turning. Where a hook or other implant is employed, rather than a screw, shaft 22 (in the form of a hook blade or other structure) will be connected to the vertebra, as by hooking it around or otherwise in contact with a pedicle, process or other vertebral part.

When the anchor 20 is connected to a bone, receiving portion 24 can be multi-axially positioned and rotated with respect to shaft 22 so that receiving portion 24 is in a desired position relative to the shaft 22 and the underlying bone. A rod can be maneuvered to the surgical site, contoured as may be desired, and then inserted into channel 53 of receiving portion 24 via mouth 55. The rod is placed in receiving portion 24 until it is adjacent or in contact with crown member 26, and in a particular embodiment adjacent or in contact with concave surface 68 of crown member 26. The rod may be pressed against surface 55 of receiving portion 24 and convex surface 68 of crown member 26, which will tend to direct the rod into channel 53, and can result in a camming action tending to push crown member 26 relatively downward onto head portion 34, and head portion 34 relatively downward onto clip 28. While not necessarily locking crown member 26, head 34 and clip 28 together, such pressure resulting from insertion of the rod may cause some biting by ridges 38 of head 34 into crown member 26, providing some stability or a pre-lock condition. Prior to final locking, receiving portion 24 is preferably capable of further multi-axial positioning.

Once the rod and receiving portion 24 are in the desired relative position with respect to shaft 22, set screw 48 is threaded down through aperture 46 in leg 40 of receiving portion 24 and into contact with the rod. Screw 48 forces the rod against crown member 26, which forces crown member 26 against head 34 and head 34 against clip 28 to lock the construct. In embodiments in which head 34 includes one or more ridges 38, such ridges may bite into crown member 26. In an embodiment in which set screw 48 has a curved or conical bottom surface, such bottom surface may tend to push the rod in a direction substantially toward intermediate portion 44 and/or base 42 of receiving portion 24. In an embodiment in which set screw 48 has a pointed bottom surface, such point(s) may bite into the rod. In an embodiment in which crown member 26 has an undulating upper surface, the rod will tend to be guided into concave portion 68 and may be guided toward intermediate portion 44 of receiving portion 24. When set screw 48 is tightened against the rod to a satisfactory degree, the rod, receiving portion 24, crown member 26 and clip 28 are locked with respect to each other.

In another embodiment, a bone anchor 220 is shown in FIGS. 13-21. Bone anchor 220 is similar in many respects to bone anchor 20, and similar parts are denoted by using numbers as above with the prefix 2. Anchor 220 includes a shaft portion 222, a receiving portion 224, and a clip 228. Shaft 222 is an elongated piece having one or more threads 230 on at least a portion, e.g. a relatively lower portion. Thread 230 may be a cancellous thread, of a configuration suited to implantation into a vertebra or similar bone. Thread 230 may be self-tapping or intermittent, or may have more than one crest winding about shaft 222, or of other appropriate configurations. A neck 232 at a relatively upper portion of shaft 222 is provided. Neck 232 may be above thread 230, or may also include thread(s) or a threaded portion. Shaft portion 222 further includes a head portion 234. Head portion 234 has a part spherical underside in one embodiment, and an imprint 236 in a top of head 234. Imprint 236 may be hexagonal, hexalobed, or of other appropriate shape.

The depicted embodiment of receiving portion 224 is substantially C-shaped, having an upper leg 240, a base 242, and an intermediate portion 244 joining them. Upper leg 240 has a threaded aperture 246 into which a set screw 248 can be threaded. Aperture 246 may have a longitudinal axis that is perpendicular to upper leg 240, or such axis may be angled with respect to upper leg 240, e.g. toward intermediate portion 244.

Base 242 includes a hole 249 therethrough. Hole 249 is at least partially substantially cylindrical in one embodiment, having longitudinal axis, a diameter at least slightly greater than the diameter of head portion 234, and a depth at least slightly greater than the height of head portion 234. In one particular embodiment, leg 240 has an underside that is obliquely angled with respect to the axis of hole 249. Thus, as a rod is loaded from the side of receiving portion 224, as further described below, the rod's general direction may be substantially perpendicular to the axis of hole 249, e.g. within ten to twenty degrees of a line perpendicular to the axis of hole 249. Near a lower end of base 242, a groove 250 is provided. Groove 250, in the illustrated embodiment, is of substantially constant depth and width, and is around all or substantially all of hole 249. Hole 249 further may include a substantially conical opening 251 at a lower end of base 242.

Clip member 228 is substantially C-shaped, with a gap 280 allowing clip 228 to be elastically expandable and contractible. Clip 228 is sized to fit at least partially within groove 250 when clip member is in an unstressed, i.e. unexpanded and uncontracted, state. Clip 228 may have at least one conical portion 282 and a substantially cylindrical portion 286. Clip 228 has an internal dimension that is at least slightly smaller than the diameter of head portion 234 of shaft portion 222, but larger than neck 232, and an external dimension that allows clip 228 to fit at least partially within groove 250. In one embodiment, the external dimension of clip 228 is at least slightly smaller than the diameter of groove 250, so that when clip 228 is within groove 250, clip 228 is in an at least slightly compressed state.

Intermediate portion 244 joins leg 240 and base 242. Taken together, leg 240, base 242 and intermediate portion 244 form substantially a C-shape, with a channel 253 substantially to one side of intermediate portion 244 and having a mouth 254 between leg 240 and base 242. A rod R (FIG. 21) may be side-loaded into receiving portion 224 by inserting it through mouth 254 toward intermediate portion 244 and into channel 253. In a particular embodiment, mouth 254 is somewhat wider than the breadth of channel 253 further within receiving portion 224. Base 242 may include a surface 255 curved or sloping somewhat toward leg 240. Channel 253 in an area adjacent to base 242 and intermediate portion 244 has a substantially cylindrical portion 256, and channel 253 communicates with hole 249. Surface 255 may meet cylindrical portion 256 at one or more ridges 257.

Figure 13:
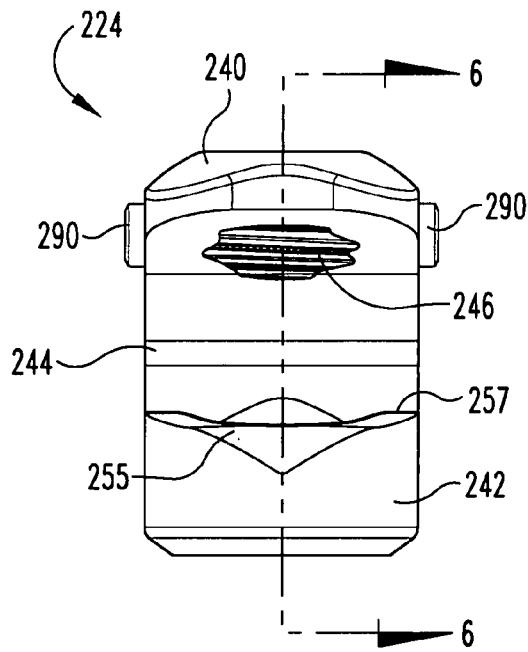
FIG. 13 is a side view of another embodiment of a receiving member.
Figure 15:
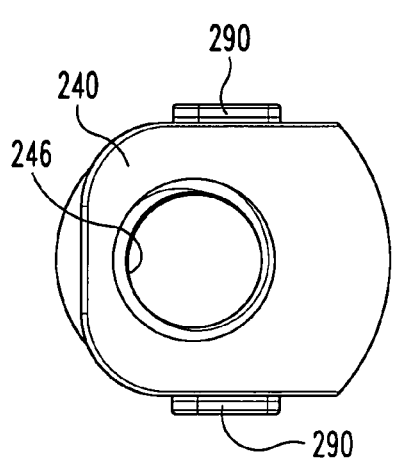
FIG. 15 is a top view of the embodiment shown in FIG. 14.
Figure 14:
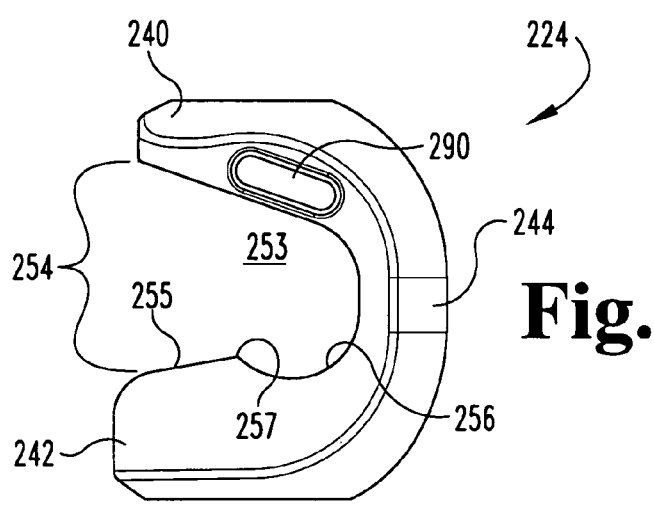
FIG. 14 is a side view of the embodiment shown in FIG. 13, rotated ninety degrees with respect to FIG. 13.
Figure 18:
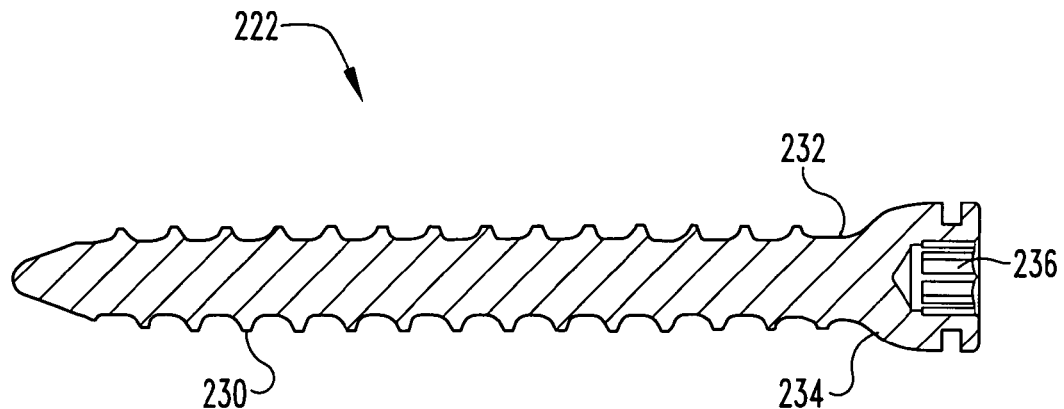
FIG. 18 is a cross-sectional view taken along the lines 18-18 in FIG. 17 and viewed in the direction of the arrows.
Figure 17:
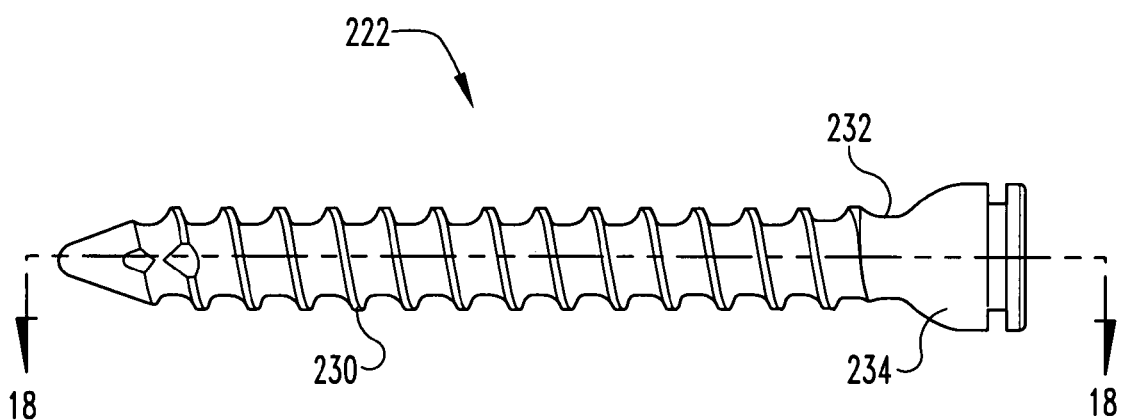
FIG. 17 is a side view of an embodiment of an anchor portion.
Figures 19, 20:
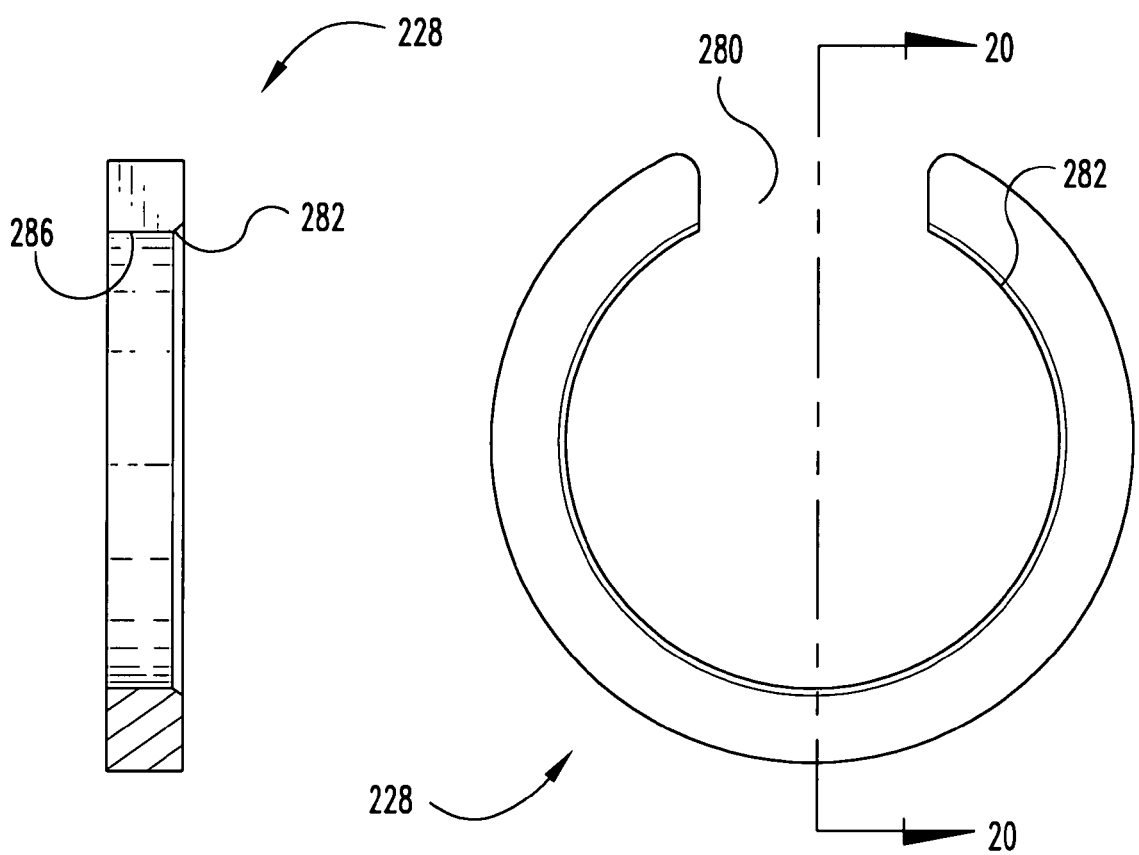
FIG. 19 is a top view of an embodiment of a clip member.
FIG. 20 is a cross-sectional view taken along the lines 20-20 in FIG. 19 and viewed in the direction of the arrows.
Figure 21:
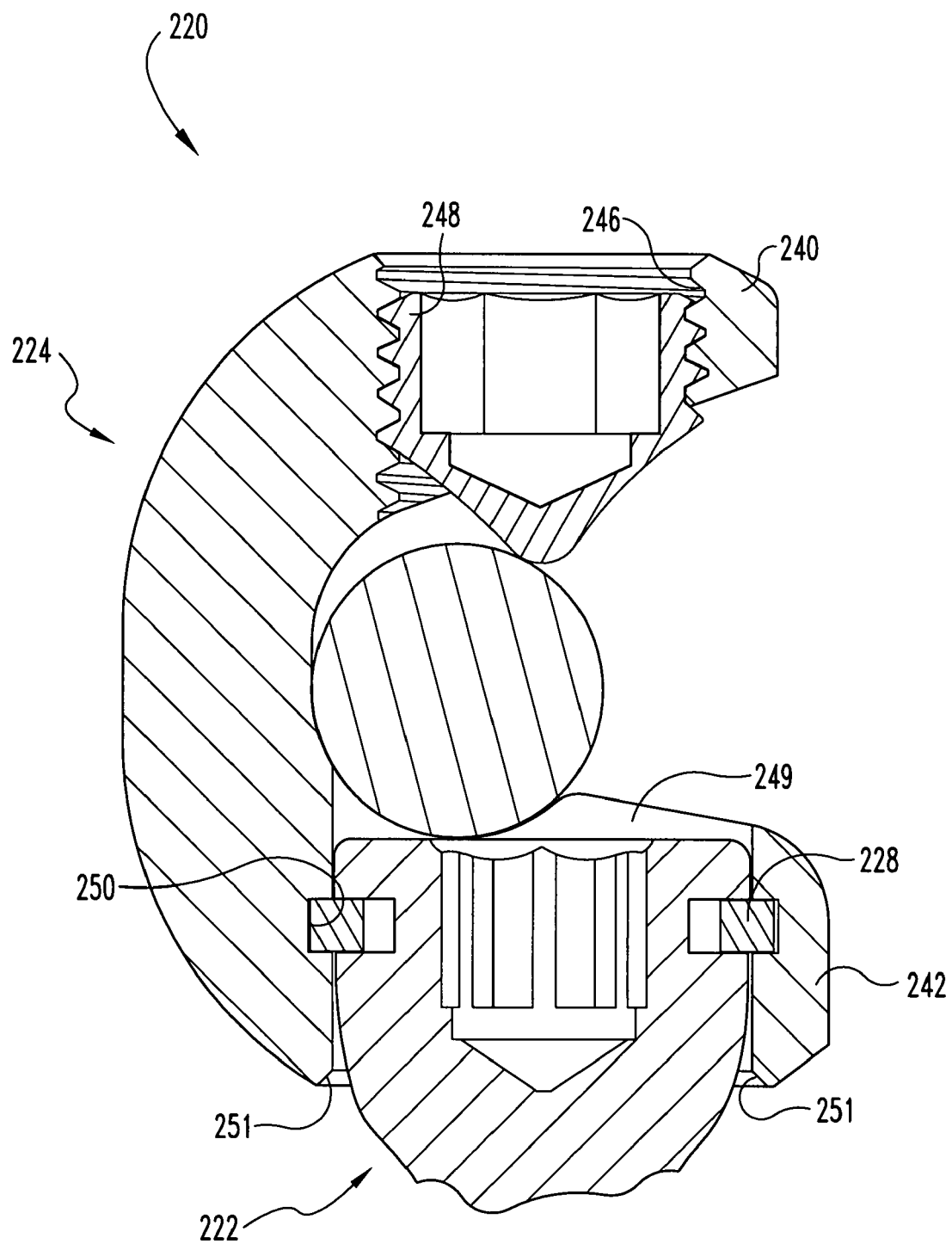
FIG. 21 is a cross-sectional view of an apparatus including embodiments as seen in FIGS. 13-20 along with a rod.

In addition to the features of the embodiment described above, receiving portion 224 may further include one or more protrusions 290 for accommodating a gripping or positioning tool. Protrusions 290 are shown in one embodiment on either side of receiving portion 224, in an area in or adjacent to upper leg 240 and intermediate portion 244. It will be seen that protrusions 290 could be in any part of receiving portion 224. Protrusions 290 shown in FIGS. 13-15 are substantially ovally-shaped and parallel to a lower surface of upper leg 240 of receiving portion 224. A holding or gripping tool (not shown) having one or more portions that can connect to or receive at least a portion of a protrusion 290. In this manner, such a tool can be used to hold, position, manipulate or otherwise work on or with screw 20.

In assembling screw 220, head portion 234 of shaft portion 222 is inserted into hole 249 via opening 251 so that at least a portion of head portion 234 emerges into channel 253. Clip 228 is drawn up around threaded portion 230 of shaft portion 222 and inserted through opening 251 into groove 250. In one embodiment, shaft portion 222 can be first inserted through clip 228, and the combination can be inserted into hole 249 so that head portion 234 is at least partially in channel 253 and clip 228 is at least partially within groove 250. In another embodiment, shaft portion 222 can first be inserted into hole 249, followed by clip 228.

Assembly of screw 220 as noted above may be done during or soon after the manufacturing process of the individual components. If done in that way, then the surgeon is provided an assembly including receiving portion 224 with shaft 222 and clip 228 connected as described above. One or more sizes of such assemblies can be provided in a kit so that the surgeon can select the appropriate assembly. Set screws, such as set screw 248, may also be provided with such assemblies. Such a set screw 248 includes external threads adapted for engagement with threaded aperture 246, and may include an internal or external imprint in or on a top surface adapted for engagement with a tool for tightening and/or loosening set screw 248. It will be seen that an internal print may be preferred as it may add nothing or a smaller amount to the overall height or profile of screw 220. Set screw 248 may further include a curved, pointed, conical or other surface at the bottom. Such a surface engages a rod within receiving portion 224 as further described below. Set screw 248 may be placed at least partially within threaded aperture 246 such that none or a very small amount of set screw 248 extends into channel 253. Alternatively, set screw may be left out of aperture 246 until a rod is inserted into receiving portion 224, and may then be inserted into aperture 246 and against the rod, as is further described below. Individual parts may also be provided to the surgeon, who can assemble the assemblies as indicated above.

Use of screw 220 is quite similar to the use described above with respect to screw 20. Additional screws 20 and/or 220 can be placed in adjacent or relatively distant bone tissue to connect to the same or additional rods. Further, other components, such as alternative screw or hook apparatus, clamps, connectors, or similar devices can be placed in connection with such rod(s) and such bone tissue(s). As may be desired by the surgeon or necessitated by the given trauma or other physical situation, bone growth materials, such as bone morphogenic protein (BMP), demineralized bone matrix (DBM), bone graft, or other substances may also be used in connection with parts of the structures described above so as to repair or correct the patient's physical situation.

Materials for set screw 48, 248 crown member 26, ridges 38 and/or the rod can be chosen so that some deformation or penetration of one part with respect to another may occur. For example, if set screw 48, 248 is provided with one or more points or edges on a bottom surface, such points or edges (or the overall material of set screw 48, 248) can be made of a harder material than the rod so that set screw 48, 248 bites into the rod as set screw 48, 248 is tightened to lock the rod within receiving portion 24, 224. As another example, if crown member 26 is of a softer material than ridges 38 of head 34, then ridges 38 may bite into the underside of crown member 26 on locking the construct.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

For example, screws 20, 220 can be sized for placement at any level of the spine. Of course, it is understood that the relative size of the components of the assembly will be modified for the particular vertebra(e) to be instrumented. For example, components may be relatively larger for lumbar or sacral placement than those for cervical placement. Likewise, the relative dimensions of shaft 22 and hole 49 and/or opening 51 in receiving portion 24 can be chosen to permit greater or lesser degrees of angulation of shaft 22 relative to receiving portion 24.

The components described above may be formed of stainless steel or other biocompatible materials, such as titanium, certain plastics or ceramics, and materials that permit bone ingrowth.

Further, while the embodiments discussed above concerns a bone screw, other bone fixation members can be adapted to implement the features disclosed herein. For instance, as noted above shaft 22, 222 could include the blade of a vertebral hook rather than a threaded element.

It is also understood that while the preferred embodiment of the invention engages a bone screw to a rod, various longitudinal members are contemplated. For example, an elongated bar can be disposed within channel 53 of receiving portion 24 to be clamped between crown member 26 and set screw 48. Such a rod or longitudinal member can be a part of a lateral connector or other piece used in orthopedic surgery. The present invention can be applied equally well to smooth rods or bars, or longitudinal members having various surface features, such as knurling or threading. Features described with respect to screw 20 can be used in connection with screw 220, and vice versa.

The entire disclosure of the United States Patent Application entitled "SIDE LOADING ADJUSTABLE BONE ANCHOR" and filed on Dec. 1, 2004, is incorporated herein by reference.

What is claimed is:

1. A side-loading vertebral anchor comprising:
   a C-shaped receiving portion having an upper leg, a base, and an intermediate portion, said receiving portion forming an open channel, said base having an aperture therethrough with a longitudinal axis and a groove communicating with said aperture, said groove substantially surrounding said aperture, said base further having a sloped or curved surface adjacent said channel, said surface ending in a ridge;
   an expandable and contractible clip member at least partially within said groove, said clip member having an internal dimension;
   an anchor portion having a head portion and a shaft portion, said head portion being at least partially within said aperture in said base of said receiving portion and adjacent said clip member, said head portion having an external dimension at least slightly larger than said internal dimension of said clip member whereby said clip member prevents passage of said head portion beyond said clip member, wherein said head of said anchor portion includes a groove, and at least a portion of said clip member is within at least a portion of said groove of said head portion;
   whereby an elongated member can be inserted from the side of said receiving portion into said channel in a direction substantially toward said intermediate portion and substantially perpendicular to said axis of said aperture in said base portion.

2. An apparatus according to claim 1, wherein said anchor portion has a longitudinal axis, and said anchor portion is rotatable around said axis with respect to said base of said receiving portion.

3. An apparatus according to claim 1, wherein said head of said anchor portion is substantially hemispherical.

4. An apparatus according to claim 1, further comprising a longitudinal member in said channel and in contact with said head, and a set screw threaded through said upper leg and against said longitudinal member whereby said longitudinal member, said anchor portion and said receiving portion are locked together.

5. A side-loading vertebral anchor comprising:
   a C-shaped receiving portion having an upper leg, a base, and an intermediate portion, said receiving portion forming an open channel, said base having an aperture therethrough with a longitudinal axis and a groove communicating with said aperture, said groove substantially surrounding said aperture, said base further having a sloped or curved surface adjacent said channel, said surface ending in a ridge;
   an expandable and contractible clip member at least partially within said groove, said clip member having an internal dimension;
   an anchor portion having a head portion and a shaft portion, said head portion being at least partially within said aperture in said base of said receiving portion and adjacent said clip member, said head portion having an external dimension at least slightly larger than said internal dimension of said clip member whereby said clip member prevents passage of said head portion beyond said clip member, wherein said head of said anchor portion contacts an upper surface of said clip member, whereby said anchor portion is multi-axially rotatable with respect to said base; and
   a crown member at least partially within said aperture of said base, said crown member having an upper undulating portion including a top surface facing said upper leg of said receiving portion, a lower portion and an aperture through said upper and lower portions, said top surface of said undulating portion having a substantially cylindrical convex top surface portion to one side of said undulating portion and a substantially cylindrical concave top surface portion to the other side of said undulating portion, said crown member aperture having a substantially spherical lower portion, wherein said substantially spherical lower portion is adjacent said head of said anchor portion; and
   whereby an elongated member can be inserted from the side of said receiving portion into said channel in a direction substantially toward said intermediate portion and substantially perpendicular to said axis of said aperture in said base portion.

6. An apparatus according to claim 5, wherein a portion of said crown member extends into said channel.

7. An apparatus according to claim 5, further comprising a longitudinal member in said channel and in contact with said crown member, and a set screw threaded through said upper leg and against said longitudinal member whereby said longitudinal member, said crown member, said anchor portion and said receiving portion are locked together.

8. An apparatus according to claim 5, wherein said receiving portion includes at least one protrusion for accommodating a tool portion, said protrusion being substantially oval shaped and parallel to an underside of said upper leg.

9. A side-loading vertebral anchor comprising:
a C-shaped receiving portion having an upper leg, a base, and an intermediate portion, said receiving portion forming an open channel, said base having an aperture therethrough with a longitudinal axis and a groove communicating with said aperture, said groove substantially surrounding said aperture, said base further having a sloped or curved surface adjacent said channel, said surface ending in a ridge, wherein said receiving portion includes at least one indentation for receiving a tool portion, said indentation having an entry portion, a holding portion with a substantially circular part, and a corner between said holding portion and said entry portion, whereby a tool portion may be inserted through said entry portion in one direction and into said holding portion in another direction;
an expandable and contractible clip member at least partially within said groove, said clip member having an internal dimension;
an anchor portion having a head portion and a shaft portion, said head portion being at least partially within said aperture in said base of said receiving portion and adjacent said clip member, said head portion having an external dimension at least slightly larger than said internal dimension of said clip member whereby said clip member prevents passage of said head portion beyond said clip member;
whereby an elongated member can be inserted from the side of said receiving portion into said channel in a direction substantially toward said intermediate portion and substantially perpendicular to said axis of said aperture in said base portion.

10. An apparatus for attachment to a vertebra and a longitudinal member, comprising:
a bone anchor portion having a head portion, a threaded shaft and a non-threaded neck, said threaded shaft having cancellous threads suited to connection to a vertebra;
a substantially C-shaped receiving portion having a base portion, an upper leg and an intermediate portion, said receiving portion including an internally threaded aperture through said upper leg, said receiving portion further including a hole in said base portion having a longitudinal axis, said receiving portion having a channel substantially perpendicular to said axis into which a longitudinal member can be placed in said receiving portion, said receiving portion further including a groove communicating with said hole, said receiving portion further including an open hook-shaped exterior imprint for accommodating a holding tool so that a holding tool can be slid into said hook-shaped imprint;
a crown member at least partially within said hole in said receiving portion, said crown member having an upper undulating portion including a top surface facing said upper leg of said receiving portion, a lower portion and an aperture through said upper and lower portions, said top surface of said undulating portion having a substantially cylindrical convex top surface portion to one side of said undulating portion and a substantially cylindrical concave top surface portion to the other side of said undulating portion, said crown member aperture having a substantially spherical lower portion; and
a ring member around at least a portion of said bone anchor such that at least a portion of said ring member is within said groove, said ring member having an internal dimension at least slightly smaller than said head portion so that said head portion of said bone anchor portion and said ring member cannot be withdrawn from said hole of said receiving portion.

11. The apparatus of claim 10, wherein said receiving portion includes an abutment adjacent said hole and said channel that prevents said crown member from exiting said hole into said channel.

12. The apparatus of claim 10, wherein said head portion of said bone anchor portion includes at least one ridge.

13. The apparatus of claim 10, wherein said channel has a substantially cylindrical portion, and said receiving portion has a front sloped or curved surface leading into said channel, said surface ending in a ridge near said substantially cylindrical portion of said channel.

14. An apparatus according to claim 10, wherein said receiving portion includes at least one protrusion for accommodating a tool portion, said protrusion being substantially oval shaped and parallel to an underside of said leg portion.

15. An apparatus according to claim 10, wherein a longitudinal member is placed in said channel and in contact with said crown member, and further comprising a set screw threaded into said upper leg and against said longitudinal member whereby said longitudinal member, said crown member, said anchor portion and said receiving portion are locked together.

16. An apparatus for attachment to a vertebra and a longitudinal member, comprising:
a bone anchor portion having a head portion, a threaded shaft and a non-threaded neck, said threaded shaft having cancellous threads suited to connection to a vertebra;
a substantially C-shaped receiving portion having a base portion, an upper leg and an intermediate portion, said receiving portion including an internally threaded aperture through said upper leg, said receiving portion further including a hole in said base portion having a longitudinal axis, said receiving portion having a channel substantially perpendicular to said axis into which a longitudinal member can be placed in said receiving portion, said receiving portion further including a groove communicating with said hole, said receiving portion further including an open hook-shaped exterior imprint for accommodating a holding tool so that a holding tool can be slid into said hook-shaped imprint, wherein said receiving portion includes at least one indentation for receiving a tool portion, said indentation having an entry portion, a holding portion with a substantially circular part, and a corner between said holding portion and said entry portion, whereby a tool portion may be inserted through said entry portion in one direction and into said holding portion in another direction;
a crown member at least partially within said hole in said receiving portion, said crown member having an upper undulating portion, a lower portion and an aperture through said upper and lower portions, said undulating portion having a substantially cylindrical convex portion to one side of said undulating portion and a substantially cylindrical concave portion to the other side of said undulating portion, said crown member aperture having a substantially spherical lower portion; and
a ring member around at least a portion of said bone anchor such that at least a portion of said ring member is within said groove, said ring member having an internal dimension at least slightly smaller than said head portion so that said head portion of said bone anchor portion and said ring member cannot be withdrawn from said hole of said receiving portion.

17. An apparatus comprising:
a receiving member for receiving a longitudinal member, said receiving member having a channel opening to the side, an upper threaded aperture and a lower aperture each communicating with said channel, said lower aperture having a lower opening and an upper opening, said upper opening adjacent said channel, said receiving member further including a groove communicating with said lower aperture;
an anchor member having a longitudinal axis and a head with an external surface and an internal imprint, said head being at least partially inserted through said lower opening and into said lower aperture, said head further including a groove in said external surface; and
a C-shaped ring member at least partially within said groove of said receiving member and at least partially within said groove of said head, whereby said anchor member is rotatable about said axis of said anchor member with respect to said receiving member.

18. An apparatus according to claim 17, further comprising a set screw for threading into said threaded aperture of said receiving member.

19. An apparatus according to claim 18, further comprising a longitudinal member within said channel and adjacent said head, wherein threading said set screw causes said set screw to contact said longitudinal member and lock said apparatus.

20. An apparatus according to claim 18, wherein said receiving member includes at least one indentation for receiving a tool portion, said indentation having an entry portion, a holding portion with a substantially circular part, and a corner between said holding portion and said entry portion, whereby a tool portion may be inserted through said entry portion in one direction and into said holding portion in another direction.

21. An apparatus according to claim 20, wherein said receiving member includes at least one protrusion for accommodating a tool portion, said protrusion being substantially oval shaped and parallel to an upper portion of said channel.

* * * * *